United States Patent
Pelleymounter et al.

(10) Patent No.: US 7,208,577 B2
(45) Date of Patent: *Apr. 24, 2007

(54) METHODS OF INCREASING LEAN TISSUE MASS USING OB PROTEIN COMPOSITIONS

(75) Inventors: Mary Ann Pelleymounter, San Diego, CA (US); Christopher Francis Toombs, Camarillo, CA (US); Michael Benjamin Mann, Thousand Oaks, CA (US)

(73) Assignee: Amgen, Inc., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/033,600

(22) Filed: Jan. 11, 2005

(65) Prior Publication Data

US 2005/0176107 A1 Aug. 11, 2005

Related U.S. Application Data

(63) Continuation of application No. 09/859,768, filed on May 16, 2001, now abandoned, which is a continuation of application No. 09/094,931, filed on Jun. 15, 1998, now abandoned, which is a continuation of application No. 09/056,719, filed on Apr. 7, 1998, now abandoned, which is a continuation of application No. 08/561,732, filed on Nov. 22, 1995, now abandoned.

(51) Int. Cl.
*C07K 16/46* (2006.01)
*A61K 38/27* (2006.01)
*A61K 38/18* (2006.01)

(52) U.S. Cl. .................. 530/350; 530/387.1; 530/399; 424/192.1; 424/196

(58) Field of Classification Search .............. 530/350, 530/387.3; 424/192.1, 194
See application file for complete search history.

(56) References Cited

U.S. PATENT DOCUMENTS

| | | | |
|---|---|---|---|
| 4,179,337 A | 12/1979 | Davis et al. | |
| 4,925,673 A | 5/1990 | Steiner et al. | |
| 5,013,556 A | 5/1991 | Woodle et al. | |
| 5,073,627 A | 12/1991 | Curtis et al. | |
| 5,098,833 A | 3/1992 | Lasky et al. | |
| 5,116,964 A | 5/1992 | Capon et al. | |
| 5,169,318 A | 12/1992 | Levy | |
| 5,225,538 A | 7/1993 | Capon et al. | |
| 5,284,656 A | 2/1994 | Platz et al. | |
| 5,349,053 A | 9/1994 | Landolfi et al. | |
| 5,428,130 A | 6/1995 | Capon et al. | |
| 5,447,851 A | 9/1995 | Beutler et al. | |
| 5,455,165 A | 10/1995 | Capon et al. | |
| 5,480,981 A * | 1/1996 | Goodwin et al. ........... 536/23.5 | |
| 5,514,582 A | 5/1996 | Capon et al. | |
| 5,594,101 A | 1/1997 | Becker et al. | |
| 5,594,104 A | 1/1997 | Basinski et al. | |
| 5,646,040 A | 7/1997 | Kleyn et al. | |
| 5,670,625 A | 9/1997 | Baum et al. | |
| 5,714,147 A | 2/1998 | Capon et al. | |
| 5,739,277 A | 4/1998 | Presta et al. | |
| 5,935,810 A | 8/1999 | Friedman et al. | |
| 6,001,968 A | 12/1999 | Friedman et al. | |
| 6,025,325 A * | 2/2000 | Campfield et al. ............ 514/2 |
| 6,048,837 A * | 4/2000 | Friedman et al. ............ 514/2 |
| 6,350,730 B1 | 2/2002 | Friedman et al. | |

FOREIGN PATENT DOCUMENTS

| | | |
|---|---|---|
| CA | 2205572 | 12/1995 |
| CA | 2195955 | 2/1996 |
| CA | 2224646 | 1/1997 |
| CA | 2238307 | 7/1997 |
| EP | 306673 | 3/1989 |
| EP | 401384 | 12/1989 |
| EP | 362999 | 4/1990 |
| EP | 417563 | 3/1991 |
| EP | 464533 | 1/1992 |
| EP | 956862 | 12/2002 |
| WO | WO 89/10932 | 11/1989 |
| WO | WO 91/11111 | 8/1991 |
| WO | WO 92/13559 | 8/1992 |
| WO | WO 94/06476 | 3/1994 |
| WO | WO 96/03141 | 2/1996 |
| WO | WO 96/04388 | 2/1996 |
| WO | WO 96/05309 | 2/1996 |
| WO | WO 96/18412 | 6/1996 |
| WO | WO 96/22308 | 7/1996 |

(Continued)

OTHER PUBLICATIONS

Ngo et al., 1994, The Protein Folding Problem and Tertiary Structure Prediction, pp. 491-495.*

Skolnick et al., From genes to protein structure and function: novel applications of computational approaches in the genomic era, Jan. 2000, Trends in Biotech. 18(1): 34-39.*

Mikayama et al, Molecular cloning and functional expression of a cDNA encoding gycosylation-inhibition factor, Nov. 1993, Proc. Natl. Acad. Sci, USA vol. 90: 10056-10060.*

Attwood et al, The Babel of Bioinformatics, 2000, Science vol. 290 No. 5491: 471-473.*

(Continued)

*Primary Examiner*—Christina Chan
*Assistant Examiner*—Phuong Huynh
(74) *Attorney, Agent, or Firm*—Amylin Pharmaceuticals, Inc.

(57) ABSTRACT

The present invention provides methods of creating and using OB protein compositions with an antibody constant region or portion thereof fused to an OB protein. The fusion protein is created by attaching the polyamino acids to the OB protein moiety. The fusion proteins can then be used for various therapeutic uses.

4 Claims, No Drawings

FOREIGN PATENT DOCUMENTS

| WO | WO 96/31526 | 10/1996 |
| --- | --- | --- |
| WO | WO 97/00319 | 1/1997 |
| WO | WO 97/18833 | 5/1997 |
| WO | WO 97/24137 | 7/1997 |
| WO | WO 97/24440 | 7/1997 |
| WO | WO 98/28427 | 7/1998 |
| WO | WO 98/46257 | 10/1998 |
| WO | WO 99/02711 | 1/1999 |
| WO | WO 99/22764 | 5/1999 |

OTHER PUBLICATIONS

Abuchowski, A., et al., "Soluble Polymer-Enzyme Adducts," *Enzymes as Drugs* (J.S. Holcerberg and J. Roberts, eds.) 367-383 (1981).
Adjei, et al., *Int'l. J. of Pharm.*, 61:135-144 (1990).
Adjei, et al., *Pharm. Res.*, 7(6):565-569 (1990).
Ashkenazi, A., et al., *A Companion to Methods in Enzymology*, 8:104-115 (1995).
Ashkenazi, A. et al., "Protection Against Edotoxic Shock by a Tumor Necrosis Factor Receptor Immunoadhesin," *PNAS USA*, 88:10535-39 (1991).
Attwood, T., et al., "The Babel of Bioinformatics," *Science* 290(5491):471-473 (Oct. 2000).
Bachmann, et al., *Bacteriol. Rev.*, 40:116-167 (1976).
Barinaga, M. "'Obese' Protein Slims Mice," *Science*, 269:475-476 (1995).
Bennett, B. et al., "Estracellular Domain-IGG Fusion Proteins for Three Human Natriuretic Peptide Receptors," *J. BioChem.* 266:(34) 23060-67 (1991).
Braquet, et al., *J. Cardiovascular Pharm.* 13(Supp. 5):S143-S146 (1989).
Campfield, L.A., et al., "Recombinant Mouse OB Protein: Evidence for a Peripheral Signal Liking Adiposity and Central Neural Networks," *Science*, 269:54-549 (1995).
Capon, D., et al., "Designing CD4 Immunoadhesins for AIDS Therapy," *Nature*, 337:525-531 (Feb. 9, 1989).
Debs, et al., *J. Immun.*, 140(10):3482-3488 (1988).
*Devos, R., et al., "OB Protein Binds Specifically to the Choroid Plexus of Mice and Rats," *Proc. Natl. Acad. Sci. USA*, 93:5668-5673 (May 1996).
Ellison, et al., "The Nucleotide Sequence of a Human Immunoglobulin Cγ1 Gene," *Nucleic Acids Research*, 10(13):4071-4079 (1982).
Fisher, C., et al., "Treatment of Septic Shock With the Tumor Necrosis Factor Receptor:Fc Fusion Protein," *N. Engl. J. Med.*, 334:1697-17022 (1996).
Francis, *Focus on Growth Factors*, 3:4-10 (1992).
*Haak-Frendscho, M. et al., "Inhibition of Interferon-γ by an interferon-γ Receptor Immunoadhesin," *Immunology*, 79:594-599 (1993).
Halaas, et al., "Weight-Reducing Effects of the Plasma Protein Encoded by the *Obese* Gene," *Science*, 269:543-546 (1995).
Harvey, et al., *Remington's Pharmaceutical Sciences*, 18th Ed., (Mack Publishing Co., Easton, PA, ed. Gennaro 1990), p. 948-1001.
Harvill, E., et al., "An IgG3-IL2 Fusion Protein Activates Complement, Binds FcγRI, Generates LAK Activity and Shows Enhanced Binding to the High Affinity IL-2R," *Immunotechnology*, 1:95-105 (1995).
Ho, S.N., et al., "Site-Directed Mutagenesis by Overlap Extension Using the Polymerase Chain Reaction," *Gene*, 77:51-59 (1989).
Hollenbaugh, et al., *Current Protocols in Immunology*, Supp. 4:10.19.1-10.19.11 (1992).
Hubbard, et al., *Annals of Internal Medicine*, 111(3):206-212 (1989).
Imagawa, K., et al., "Structure-Function Studies of Human Leptin," *J. Biological Chem.*, 273(52):35245-49 (1998).

*Kolaczynski, J., et al., "Acute and Chronic Effects of Insulin on Leptin Production in Humans: Studies in vivo and in vitro." *Diabetes*, 45(5):699-701 (1996).
Leshner, et al., *Physiology and Behavior*, 9:281-282 (1972).
*Luoh, S-M., et al., *J. Mol. Endo.*, 18:77-85 (1997).
MacDonald, et al., *Methods in Enzymology*, 152:219-227 (1987).
Malik, F., et al., "Polyethylen Glycol (PEG)-modifided Granulocyte-Macrophage Colony-stimulating Factor (GM-CSF) with Conserved Biological Activity," *Exp. Hematol.*, 20:1028-1035 (1992).
Mark, M., et al., "Expression and Characterization of Hepatocyte Growth Factor Receptor-IgG Fusion Proteins," *J. Bio Chem.*, 267:(36) 26166-71 (1992).
Marshall, *Modern Pharmaceutics* (Marcel Dekker, Inc., NY, eds. Banker and Rhodes 1979) p. 359-427.
Mikayama, T., et al. Molecular Cloning and Functional Expression of a cDNA Encoding Glycosylation-Inhibiting Factor, Nov. 1993, *Proc. Natl. Acad. Sci., USA*, 90:10056-10060.
Murakami, T., et al., "Cloning of Rat *Obese* cDNA and Its Expression in Obese Rats," *Biochem. Biophys. Res. Comm.*, 209(3):944-952 (1995).
Newmark, et al., *J. Appl. Biochem.* 4:185-189 (1982).
Ngo, et al., The Protein Folding Problem and Tertiary Structure Prediction, pp. 491-495.
Oeswein, et al., "Aerosolization of Proteins," *Proceedings of Symposium on Respiratory Drug Delivery II*, Keystone, CO, Mar. 1990.
Pelleymounter, M.A., et al., "Effects of the *Obese* Gene Product on Body Weight Regulation in *ob/ob* Mice," *Science*, 269:540-543 (1995).
Prescott, et al., *Microbiology* (1990, Wm. C. Brown Publ., Dubuque, IA 52001) p. 599-602.
*Remington's Pharmaceutical Sciences*, 18th Ed. (1990, Mack Publishing Co., Easton, PA 18042) p. 1435-1712 (Table of Contents Provided).
*Remington's Pharmaceutical Sciences*, 18th Ed. (1990, Mack Publishing Co., Easton, PA 18042) Chapter 89 (Table of Contents Provided).
Sambrook, et al., *Molecular Cloning: A Laboratory Manual*, 2d Edition, Cold Spring Harbor Laboratory Press, Cold Spring Harbor, NY (Table of Contents Provided).
Skolnick, et al., "From Genes to Protein Structure and Function: Novel Applications of Computational Approaches in the Genomic Era," *Trends in Biotech.*, 18(1):34-39 (Jan. 2000).
Shin, et al., *Intern. Rev. Immunol.*, 10:177-186 (1993).
Smith, et al., *J. Clin. Invest.*, 84:1145-1154 (1989).
Stephens, T., et al., "Life Without Neuropeptide Y," *Nature*, 377:530-532 (1995).
*Stryer, L., et al., *Biochemistry*, Third Edition, W H Freeman Company, New York, p. 31-33 (1998).
Sussman, et al., *C.R. Acad. Sci.*, 254(8):1517-1519 (1962).
Van Zee, K. et al., "Protection Against Lethal *Escherichia coli* Bacteremia in Baboons (*Papio anubis*) by Pretreatment with a 55-kDa TNF Receptor (CD120a)-Ig Fusion Protein, Ro 45-2081," *J. Immunology*, 156:2221-2230 (1996).
*Verma, I. et al., "Gene-Therapy—Promises, Problems, and Prospects," *Nature*, 389:239-242 (Sep. 18, 1997).
Voet, D., et al., *Biochemistry*. New York: John Wiley and Sons 1990, pp. 126-234.
*Zhang, et al., Correction at *Nature*, 374:479 (1995).
Zhang, Y., et al., "Positional Cloning of the Mouse *Obese* Gene and its Human Homologue," *Nature*, 372:425-432 (1994).
Zheng, X. et al., "Administration of Noncytolytic IL-10/Fc in Murine Models of Lipopolysaccharide-Induced Septic Shock and Allogeneic Islet Transplantation," *The Journal of Immunology*, 154:5590-5600 (1995).

* cited by examiner

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
    (A) LENGTH: 491 base pairs
    (B) TYPE: nucleic acid
    (C) STRANDEDNESS: double
    (D) TOPOLOGY: linear (ii) MOLECULE TYPE: DNA (genomic)

(ix) FEATURE:
    (A) NAME/KEY: CDS
    (B) LOCATION: 41..481

(xi) SEQUENCE DESCRIPTION: SEQ ID NO: 1:

```
TCTAGATTTG AGTTTTAACT TTTAGAAGGA GGAATAACAT ATG GTA CCG ATC CAG        55
                                            Met Val Pro Ile Gln
                                             1               5

AAA GTT CAG GAC GAC ACC AAA ACC TTA ATT AAA ACG ATC GTT ACG CGT        103
Lys Val Gln Asp Asp Thr Lys Thr Leu Ile Lys Thr Ile Val Thr Arg
                 10                  15                  20

ATC AAC GAC ATC AGT CAC ACC CAG TCG GTC TCC GCT AAA CAG CGT GTT        151
Ile Asn Asp Ile Ser His Thr Gln Ser Val Ser Ala Lys Gln Arg Val
             25                  30                  35

ACC GGT CTG GAC TTC ATC CCG GGT CTG CAC CCG ATC CTA AGC TTG TCC        199
Thr Gly Leu Asp Phe Ile Pro Gly Leu His Pro Ile Leu Ser Leu Ser
         40                  45                  50

AAA ATG GAC CAG ACC CTG GCT GTA TAC CAG CAG GTG TTA ACC TCC CTG        247
Lys Met Asp Gln Thr Leu Ala Val Tyr Gln Gln Val Leu Thr Ser Leu
 55                  60                  65

CCG TCC CAG AAC GTT CTT CAG ATC GCT AAC GAC CTC GAG AAC CTT CGC        295
Pro Ser Gln Asn Val Leu Gln Ile Ala Asn Asp Leu Glu Asn Leu Arg
 70                  75                  80                  85

GAC CTG CTG CAC CTG CTG GCA TTC TCC AAA TCC TGC TCC CTG CCG CAG        343
Asp Leu Leu His Leu Leu Ala Phe Ser Lys Ser Cys Ser Leu Pro Gln
                 90                  95                 100

ACC TCA GGT CTT CAG AAA CCG GAA TCC CTG GAC GGG GTC CTG GAA GCA        391
Thr Ser Gly Leu Gln Lys Pro Glu Ser Leu Asp Gly Val Leu Glu Ala
             105                 110                 115

TCC CTG TAC AGC ACC GAA GTT GTT GCT CTG TCC CGT CTG CAG GGT TCC        439
Ser Leu Tyr Ser Thr Glu Val Val Ala Leu Ser Arg Leu Gln Gly Ser
```

```
                   120                 125                 130
CTT CAG GAC ATC CTT CAG CAG CTG GAC GTT TCT CCG GAA TGT              481
Leu Gln Asp Ile Leu Gln Gln Leu Asp Val Ser Pro Glu Cys
    135                 140                 145

TAATGGATCC                                                           491

(2) INFORMATION FOR SEQ ID NO: 2:

(i) SEQUENCE CHARACTERISTICS:
        (A) LENGTH: 147 amino acids
        (B) TYPE: amino acid
        (D) TOPOLOGY: linear (ii) MOLECULE TYPE: protein (xi) SEQUENCE DESCRIPTION: SEQ ID NO: 2:

Met Val Pro Ile Gln Lys Val Gln Asp Asp Thr Lys Thr Leu Ile Lys
 1               5                  10                  15

Thr Ile Val Thr Arg Ile Asn Asp Ile Ser His Thr Gln Ser Val Ser
            20                  25                  30

Ala Lys Gln Arg Val Thr Gly Leu Asp Phe Ile Pro Gly Leu His Pro
        35                  40                  45

Ile Leu Ser Leu Ser Lys Met Asp Gln Thr Leu Ala Val Tyr Gln Gln
    50                  55                  60

Val Leu Thr Ser Leu Pro Ser Gln Asn Val Leu Gln Ile Ala Asn Asp
65                  70                  75                  80

Leu Glu Asn Leu Arg Asp Leu Leu His Leu Leu Ala Phe Ser Lys Ser
                85                  90                  95

Cys Ser Leu Pro Gln Thr Ser Gly Leu Gln Lys Pro Glu Ser Leu Asp
            100                 105                 110

Gly Val Leu Glu Ala Ser Leu Tyr Ser Thr Glu Val Val Ala Leu Ser
        115                 120                 125

Arg Leu Gln Gly Ser Leu Gln Asp Ile Leu Gln Gln Leu Asp Val Ser
    130                 135                 140

Pro Glu Cys
145

(2) INFORMATION FOR SEQ ID NO: 3:

(i) SEQUENCE CHARACTERISTICS:
        (A) LENGTH: 454 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 4..444

(xi) SEQUENCE DESCRIPTION: SEQ ID NO: 3:

CAT ATG GTA CCG ATC CAG AAA GTT CAG GAC GAC ACC AAA ACC TTA ATT      48
    Met Val Pro Ile Gln Lys Val Gln Asp Asp Thr Lys Thr Leu Ile
     1               5                  10                  15

AAA ACG ATC GTT ACG CGT ATC AAC GAC ATC AGT CAC ACC CAG TCG GTG      96
Lys Thr Ile Val Thr Arg Ile Asn Asp Ile Ser His Thr Gln Ser Val
                    20                  25                  30

AGC TCT AAA CAG CGT GTT ACA GGC CTG GAC TTC ATC CCG GGT CTG CAC      144
Ser Ser Lys Gln Arg Val Thr Gly Leu Asp Phe Ile Pro Gly Leu His
            35                  40                  45
```

```
CCG ATC CTG ACC TTG TCC AAA ATG GAC CAG ACC CTG GCT GTA TAC CAG      192
Pro Ile Leu Thr Leu Ser Lys Met Asp Gln Thr Leu Ala Val Tyr Gln
         50                  55                  60

CAG ATC TTA ACC TCC ATG CCG TCC CGT AAC GTT CTT CAG ATC TCT AAC      240
Gln Ile Leu Thr Ser Met Pro Ser Arg Asn Val Leu Gln Ile Ser Asn
     65                  70                  75

GAC CTC GAG AAC CTT CGC GAC CTG CTG CAC GTG CTG GCA TTC TCC AAA      288
Asp Leu Glu Asn Leu Arg Asp Leu Leu His Val Leu Ala Phe Ser Lys
 80              85                  90                  95

TCC TGC CAC CTG CCA TGG GCT TCA GGT CTT GAG ACT CTG GAC TCT CTG      336
Ser Cys His Leu Pro Trp Ala Ser Gly Leu Glu Thr Leu Asp Ser Leu
                100                 105                 110

GGC GGG GTC CTG GAA GCA TCC GGT TAC AGC ACC GAA GTT GTT GCT CTG      384
Gly Gly Val Leu Glu Ala Ser Gly Tyr Ser Thr Glu Val Val Ala Leu
            115                 120                 125

TCC CGT CTG CAG GGT TCC CTT CAG GAC ATG CTT TGG CAG CTG GAC CTG      432
Ser Arg Leu Gln Gly Ser Leu Gln Asp Met Leu Trp Gln Leu Asp Leu
        130                 135                 140

TCT CCG GGT TGT TAATGGATCC                                           454
Ser Pro Gly Cys
    145
```

(2) INFORMATION FOR SEQ ID NO: 4:

(i) SEQUENCE CHARACTERISTICS:
        (A) LENGTH: 147 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Val Pro Ile Gln Lys Val Gln Asp Asp Thr Lys Thr Leu Ile Lys
 1               5                  10                  15

Thr Ile Val Thr Arg Ile Asn Asp Ile Ser His Thr Gln Ser Val Ser
            20                  25                  30

Ser Lys Gln Arg Val Thr Gly Leu Asp Phe Ile Pro Gly Leu His Pro
        35                  40                  45

Ile Leu Thr Leu Ser Lys Met Asp Gln Thr Leu Ala Val Tyr Gln Gln
     50                  55                  60

Ile Leu Thr Ser Met Pro Ser Arg Asn Val Leu Gln Ile Ser Asn Asp
65                  70                  75                  80

Leu Glu Asn Leu Arg Asp Leu Leu His Val Leu Ala Phe Ser Lys Ser
                85                  90                  95

Cys His Leu Pro Trp Ala Ser Gly Leu Glu Thr Leu Asp Ser Leu Gly
                100                 105                 110

Gly Val Leu Glu Ala Ser Gly Tyr Ser Thr Glu Val Val Ala Leu Ser
            115                 120                 125

Arg Leu Gln Gly Ser Leu Gln Asp Met Leu Trp Gln Leu Asp Leu Ser
        130                 135                 140

Pro Gly Cys
145
```

(2) INFORMATION FOR SEQ ID NO: 5:

(i) SEQUENCE CHARACTERISTICS:
        (A) LENGTH: 491 base pairs
        (B) TYPE: nucleic acid
        (C) STRANDEDNESS: double
        (D) TOPOLOGY: linear -continued (ii) MOLECULE TYPE: DNA (genomic)

(xi) SEQUENCE DESCRIPTION: SEQ ID NO: 5:

```
GGATCCATTA ACATTCCGGA GAAACGTCCA GCTGCTGAAG GATGTCCTGA AGGGAACCCT        60
GCAGACGGGA CAGAGCAACA ACTTCGGTGC TGTACAGGGA TGCTTCCAGG ACCCCGAGG        120
CGCGAAGGTT CTCGAGGTCG TTAGCGATCT GAAGAACGTT CTGGGACGGC AGGGAGGTT        180
ACACCTGCTG GAGGTCGCGA AGGTTCTCGA GGTCGTTAGC GATCTGAAGA ACGTTCTGG        240
ACGGCAGGGA GGTTAACACC TGCTGGTATC AGACCAGGGT CTGGTCCATT TTGGCAAAG        300
TTAGGATCGG GTGCAGACCC GGGATGAAGT CCAGACCGGT AACACGCTGT TTAGCGGAG        360
CCGACTGGGT GTGACTGATG TCGTTGATAC GCGTAACGAT CGTTTTAATT AAGGTTGTT        420
TGTCGTCCTG AACTTTCTGG ATCGGTACCA TATGTTATTC CTCCTTCTAA AAGTTAAAA        480
TCAAATCTAG A                                                           491
```

(2) INFORMATION FOR SEQ ID NO: 6:

(i) SEQUENCE CHARACTERISTICS:
        (A) LENGTH: 453 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 6:

```
GGATCCATTA ACAACCCGGA GACAGGTCCA GCTGCCAAGC ATGTCCTAAG GGAACCCTGC        60
AGACGGGACA GAGCAACAAC TTCGGTTGCT GTAACCGGAT GCTTCCAGGA CCCCGCCCA       120
AGAGTCCAGA GTCTCAAGAC CTGAAGCCCA TGGCAGGTGG CAGGATTTGG AGAATGCCA       180
CACGTGCAGC AGGTCGCGAA GGTTCTCGAG GTCGTTAGAG ATCTGAAGAA CGTTACGGG       240
CGGCATGGAG GTTAAGATCT GCTGGTATAC AGCCAGGGTC TGGTCCATTT TGGACAAGG       300
CAGGATCGGG TGCAGACCCG GGATGAAGTC CAGGCCTGTA ACACGCTGTT TAGAGCTCA       360
CGACTGGGTG TGACTGATGT CGTTGATACG CGTAACGATC GTTTTAATTA AGGTTTTGG       420
GTCGTCCTGA ACTTTCTGGA TCGGTACCAT ATG                                   453
```

METHODS OF INCREASING LEAN TISSUE MASS USING OB PROTEIN COMPOSITIONS

CROSS-REFERENCE TO RELATED APPLICATIONS

This Application is a Continuation of U.S. patent application Ser. No. 09/859,768, filed May 16, 2001 and now abandoned, which is a continuation of U.S. application Ser. No. 09/094,931, filed Jun. 15, 1998 and now abandoned, which is a continuation of U.S. application Ser. No. 09/056,719, filed Apr. 7, 1998 and now abandoned, which is a continuation of U.S. application Ser. No. 08/561,732 filed on Nov. 22, 1995, and now abandoned. Priority to each of these Applications is claimed under 35 U.S.C. §§ 119 and 120. These applications are also incorporated herein by reference.

FIELD OF THE INVENTION

The present invention relates to methods of using OB protein compositions for increasing lean tissue mass.

BACKGROUND

Although the molecular basis for obesity is largely unknown, the identification of the "OB gene" and protein encoded ("OB protein") has shed some light on mechanisms the body uses to regulate body fat deposition. Zhang, et al., Nature 372: 425–439 (1994); see also, the Correction at Nature 374: 479 (1995). The OB protein is active in vivo in both ob/ob mutant mice (mice obese due to a defect in the production of the OB gene product) as well as in normal, wild type mice. The biological activity manifests itself in, among other things, weight loss. See generally, Barinaga, "Obese" Protein Slims Mice, Science 269: 475–476 (1995).

The other biological effects of OB protein are not well characterized. It is known, for instance, that in ob/ob mutant mice, administration of OB protein results in a decrease in serum insulin levels, and serum glucose levels. It is also known that administration of OB protein results in a decrease in body fat. This was observed in both ob/ob mutant mice, as well as non-obese normal mice. Pelleymounter et al., Science 269: 540–543 (1995); Halaas et al., Science 269: 543–546 (1995). See also, Campfield et al., Science 269: 546–549 (1995) (Peripheral and central administration of microgram doses of OB protein reduced food intake and body weight of ob/ob and diet-induced obese mice but not in db/db obese mice.) In none of these reports have toxicities been observed, even at the highest doses.

The elucidation of other biological effects of the OB protein, particularly on animals which may not benefit from or may not need weight reduction, will provide additional uses for the OB protein.

One such use, as provided by the present invention, is in the increase in lean tissue mass.

Of course, modulation of diet and exercise is one way to increase muscle size. There are also compositions used to increase lean mass. Current compositions thought to increase lean tissue mass include anabolic steroids, such as testosterone and derivatives, and human growth hormone. These are noted to have undesirable side effects however. (The summary below is fully explained in Remington's Pharmaceutical Sciences, 18$^{th}$ Ed. (1990, Mack Publishing Co., Easton. PA 18042) Chapter 50, at pages 948–1001.))

Human growth hormone, such as Protropin and Somatropin are noted to frequently caused hypercalciuria, which usually regresses in 2 to 3 months. Hyperglycemia and frank diabetes mellitus are also noted to occur. Myalgia and early morning headaches are noted to be relatively frequent, and occasionally cases of hypothyroidism and supersaturation of cholesterol in bile may occur. If the epiphyses are closed, the hormone should not be used because continued stimulation of growth of the phalanges and jawbone, but not other bones, can cause abnormal body proportions.

Anabolic steroids increase athletic performance and aggressiveness. Their use has been condemned by the American College of Sports Medicine. Female performance is improved, but at the expense of virilization and acne vulgaris. Androgens cause hirsutism, deepening or hoarseness of the voice, precocious puberty and epiphyseal closure in immature males, increased libido (in both male and female) priapism, oligospermia, and testicular atrophy, enlargement of the clitoris in the female, flushing, decreased ejaculatory volume and sperm population, gynecomastia, hypersensitivity, acne, weight gain, edema and hypercalcemia, Prolonged use increases aggressiveness, sometimes enormously, and many assaults are stated to be attributable to androgen abuse. Paranoia-like and other psychotic behavior has been reported. Biliary statis and jaundice occur. There have been a few cases reported of hepatoma following long term therapy.

It is therefore desirable to have a therapeutic or cosmetic composition which increases lean tissue mass without side effects seen in the presently available drugs.

SUMMARY OF THE INVENTION

The present invention stems from the observation that administration of OB protein to non-obese as well as obese animals results in an increase of lean tissue mass. Thus, OB protein has the capacity to act, in addition to acting as a weight reducing agent, as an agent affecting lean tissue mass. As such, numerous lean tissue-mass increasing therapies are contemplated, even for patients who would not necessarily benefit from weight reduction. Thus, one aspect of the present invention is the use of OB protein (or analogs or derivatives thereof) for increasing lean tissue mass.

In another aspect, the present invention relates to methods of treating diabetes, and reducing the levels of insulin necessary for the treatment of diabetes. The increase in lean tissue mass, with concomitant decrease in fat tissue mass, increases sensitivity to insulin. Therefore, the present methods relate to use of OB protein (or analogs or derivatives thereof) for decreasing the amount of insulin necessary for the treatment of diabetes.

DETAILED DESCRIPTION

As stated above, the methods of the present invention are those for increasing lean tissue mass in an individual. This increase in lean tissue mass has been observed to accompany a decrease in fat mass. Thus, even if administration of OB protein (or analogs or derivatives thereof) does not result in a desired amount of weight loss, administration of OB protein may be useful to reconfigure body mass in reducing body fat, while increasing lean mass.

Additionally, the increase in lean tissue mass may make an individual more sensitive to insulin, and thus the present methods of using OB protein (or analogs or derivatives thereof) are also related to increasing insulin sensitivity in a diabetic patient. While the precise mode of action is uncertain, lean tissue (e.g., muscle), as compared to fat tissue, may be more sensitive to the effects of insulin. Therefore, an increase in lean tissue may make available more cells which are sensitive to insulin. Further, elimination of fat (e.g., adipose) tissue may have the additional benefit of providing lean tissue with additional exposure to the peripheral circulation, where circulating insulin is found. It is therefore another aspect of the present invention that a method of increasing sensitivity to insulin is provided. Put another way, a method of decreasing the dosage of insulin needed by a diabetic is thus also provided.

The increase in lean tissue may be an increase in muscle tissue. Such increase is observed to be an overall increase, rather than localized to particular areas (e.g., Examples 1 and 2 below). As such, overall strength may increase. With the increase in overall strength, other benefits may result, such as a decrease in bone resorption, with the potential to reverse or improve frailty such as osteoporosis. In patients desiring improved athletic performance, an increase in overall strength may also provide as such. There may be an increase in red blood cell production or effectiveness, and an increase in oxygenated blood. As such, mental as well as physical performance may be improved.

The OB protein may be selected from recombinant murine set forth below (SEQ ID NO: 2), or recombinant human protein as set forth in Zhang et al., Nature, supra, (herein incorporated by reference) or those lacking a glutaminyl residue at position 28. (See Zhang et al., Nature, supra, at page 428.) One may also use the recombinant human OB protein analog as set forth in SEQ ID NO: 4, which contains 1) an arginine in place of lysine at position 35 and 2) a leucine in place of isoleucine at position 74. (A shorthand abbreviation for this analog is the recombinant human R->$K^{35}$, L->$I^{74}$.) The amino acid sequences for the recombinant human analog and recombinant murine proteins are set forth below with a methionyl residue at the −1 position, however, as with any of the present OB proteins and analogs, the methionyl residue may be absent.

The murine protein is substantially homologous to the human protein, particularly as a mature protein, and, further, particularly at the N-terminus. One may prepare an analog of the recombinant human protein by altering (such as substituting amino acid residues), in the recombinant human sequence, the amino acids which diverge from the murine sequence. Because the recombinant human protein has biological activity in mice, such analog would likely be active in humans. For example, using a human protein having a lysine at residue 35 and an isoleucine at residue 74 according to the numbering of SEQ ID NO: 4, wherein the first amino acid is valine, and the amino acid at position 146 is cysteine, one may substitute with another amino acid one or more of the amino acids at positions 32, 35, 50, 64, 68, 71, 74, 77, 89, 97, 100, 105, 106, 107, 108, 111, 118, 136, 138, 142, and 145. One may select the amino acid at the corresponding position of the murine protein (SEQ ID NO: 2), or another amino acid.

One may further prepare "consensus" molecules based on the rat OB protein sequence. Murakami et al., Biochem. Biophys. Res. Comm. 209: 944–952 (1995) herein incorporated by reference. Rat OB protein differs from human OB protein at the following positions (using the numbering of SEQ ID NO: 4): 4, 32, 33, 35, 50, 68, 71, 74, 77, 78, 89, 97, 100, 101, 102, 105, 106, 107, 108, 111, 118, 136, 138 and 145. One may substitute with another amino acid one or more of the amino acids at these divergent positions. The positions in bold print are those in which the murine OB protein as well as the rat OB protein are divergent from the human OB protein, and thus, are particularly suitable for alteration. At one or more of these positions, one may substitute an amino acid from the corresponding rat OB protein, or another amino acid.

The positions from both rat and murine OB protein which diverge from the mature human OB protein are: 4, 32, 33, 35, 50, 64, 68, 71, 74, 77, 78, 89, 97, 100, 102, 105, 106, 107, 108, 111, 118, 136, 138, 142, and 145. A human OB protein according to SEQ ID NO: 4 (with lysine at position 35 and isoleucine at position 74) having one or more of the above amino acids deleted or replaced with another amino acid, such as the amino acid found in the corresponding rat or murine sequence, may also be effective.

In addition, the amino acids found in rhesus monkey OB protein which diverge from the mature human OB protein are (with identities noted in parentheses in one letter amino acid abbreviation): 8 (S), 35 (R), 48 (V), 53 (O), 60 (I), 66 (I), 67 (N), 68 ((L), 89 (L), 100 (L), 108 (E), 112 (D), and 118 (L). Since (as described in Example 2, below) the recombinant human OB protein is active in cynomolgus monkeys, a human OB protein according to SEQ ID NO: 4 (with lysine at position 35 and isoleucine at position 74) having one or more of the rhesus monkey divergent amino acids replaced with another amino acid, such as the amino acids in parentheses, may be effective. It should be noted that certain rhesus divergent amino acids are also those found in the above murine species (positions 35, 68, 89, 100 and 112). Thus, one may prepare a murine/rhesus/human consensus molecule having (using the numbering of SEQ ID NO: 4 having a lysine at position 35 and an isoleucine at position 74) having one or more of the amino acids at positions replaced by another amino acid: 4, 8, 32, 33, 35, 48, 50, 53, 60, 64, 66, 67, 68, 71, 74, 77, 78, 89, 97, 100, 102, 105, 106, 107, 108, 111, 112, 118, 136, 138, 142, and 145.

Other analogs may be prepared by deleting a part of the protein amino acid sequence. For example, the mature protein lacks a leader sequence (−22 to −1). One may prepare the following truncated forms of human OB protein molecules (using the numbering of SEQ ID NO: 4):

(a) amino acids 98–146
(b) amino acids 1–32
(c) amino acids 40–116
(d) amino acids 1–99 and (connected to) 112–146
(e) amino acids 1–99 and (connected to) 112–146 having one or more of amino acids 100–111 placed between amino acids 99 and 112.

In addition, the truncated forms may also have altered one or more of the amino acids which are divergent (in the rhesus, rat or murine OB protein) from human OB protein. Furthermore, any alterations may be in the form of altered amino acids, such as peptidomimetics or D-amino acids.

The present protein (herein the term "protein" is used to include "peptide" and OB analogs, such as those recited infra, unless otherwise indicated) may also be derivatized by the attachment of one or more chemical moieties to the protein moiety. The chemically modified derivatives may be further formulated for intraarterial, intraperitoneal, intramuscular, subcutaneous, intravenous, oral, nasal, pulmonary, topical or other routes of administration. Chemical modification of biologically active proteins has been found to provide additional advantages under certain circumstances, such as increasing the stability and circulation time of the therapeutic protein and decreasing immunogenicity. See U.S. Pat. No. 4,179,337, Davis et al., issued Dec. 18, 1979. For a review, see Abuchowski et al., in Enzymes as Drugs. (J. S. Holcerberg and J. Roberts, eds. pp. 367–383 (1981)). A review article describing protein modification and fusion proteins is Francis, Focus on Growth Factors 3: 4–10

(May 1992) (published by Mediscript, Mountview Court, Friem Barnet Lane, London N20, OLD, UK).

The chemical moieties suitable for derivatization may be selected from among various water soluble polymers. The polymer selected should be water soluble so that the protein to which it is attached does not precipitate in an aqueous environment, such as physiological environment. Preferably, for therapeutic use of the end-product preparation, the polymer will be pharmaceutically acceptable. One skilled in the art will be able to select the desired polymer based on such considerations as whether the polymer/protein conjugate will be used therapeutically, and if so, the desired dosage, circulation time, resistance to proteolysis, and other considerations. For the present proteins and peptides, the effectiveness of the derivatization may be ascertained by administering the derivative, in the desired form (i.e., by osmotic pump, or, more preferably, by injection or infusion, or, further formulated for oral, pulmonary or nasal delivery, for example), and observing biological effects as described herein.

The water soluble polymer may be selected from the group consisting of, for example, polyethylene glycol, copolymers of ethylene glycol/propylene glycol, carboxymethylcellulose, dextran, polyvinyl alcohol, polyvinyl pyrolidone, poly-1,3-dioxolane, poly-1,3,6-trioxane, ethylene/maleic anhydride copolymer, polyaminoacids (either homopolymers or random or non-random copolymers), and dextran or poly(n-vinyl pyrolidone)polyethylene glycol, propylene glycol homopolymers, polypropylene oxide/ethylene oxide co-polymers, polyoxyethylated polyols, polystyrenemaleate and polyvinyl alcohol. Polyethylene glycol propionaldenhyde may have advantages in manufacturing due to its stability in water.

Fusion proteins may be prepared by attaching polyaminoacids to the OB protein (or analog) moiety. For example, the polyamino acid may be a carrier protein which serves to increase the circulation half life of the protein. For the present therapeutic or cosmetic purposes, such polyamino acid should be those which do not crease neutralizing antigenic response, or other adverse response. Such polyamino acid may be selected from the group consisting of serum album (such as human serum albumin), an antibody or portion thereof (such as an antibody constant region, sometimes called "$F_c$") or other polyamino acids. As indicated below, the location of attachment of the polyamino acid may be at the N-terminus of the OB protein moiety, or other place, and also may be connected by a chemical "linker" moiety to the OB protein.

The polymer may be of any molecular weight, and may be branched or unbranched. For polyethylene glycol, the preferred molecular weight is between about 2 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

The number of polymer molecules so attached may vary, and one skilled in the art will be able to ascertain the effect on function. One may mono-derivatize, or may provide for a di-, tri-, tetra- or some combination of derivatization, with the same or different chemical moieties (e.g., polymers, such as different weights of polyethylene glycols). The proportion of polymer molecules to protein (or peptide) molecules will vary, as will their concentrations in the reaction mixture. In general, the optimum ratio (in terms of efficiency of reaction in that there is no excess unreacted protein or polymer) will be determined by factors such as the desired degree of derivatization (e.g., mono, di-, tri-, etc.), the molecular weight of the polymer selected, whether the polymer is branched or unbranched, and the reaction conditions.

The chemical moieties should be attached to the protein with consideration of effects on functional or antigenic domains of the protein. There are a number of attachment methods available to those skilled in the art. E.g., EP 0 401 384 herein incorporated by reference (coupling PEG to G-CSF), see also Malik et al., Exp. Hematol. 20: 1028–1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residue. Those having a free carboxyl group may include aspartic acid residues, glutamic acid residues, and the C-terminal amino acid residue. Sulfhydrl groups may also be used as a reactive group for attaching the polyethylene glycol molecule(s). Preferred for therapeutic purposes is attachment at an amino group, such as attachment at the N-terminus or lysine group. Attachment at residues important for receptor binding should be avoided if receptor binding is desired.

One may specifically desire N-terminally chemically modified protein. Using polyethylene glycol as an illustration of the present compositions, one may select from a variety of polyethylene glycol molecules (by molecular weight, branching, etc.), the proportion of polyethylene glycol molecules to protein molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective N-terminal chemical modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved. For example, one may selectively N-terminally pegylate the protein by performing the reaction at a pH which allows one to take advantage of the $pK_a$ differences between the $\epsilon$-amino group of the lysine residues and that of the $\alpha$-amino group of the N-terminal residue of the protein. By such selective derivatization, attachment of a water soluble polymer to a protein is controlled: the conjugation with the polymer takes place predominantly at the N-terminus of the protein and no significant modification of other reactive groups, such as the lysine side chain amino groups, occurs. Using reductive alkylation, the water soluble polymer may be of the type described above, and should have a single reactive aldehyde for coupling to the protein. Polyethylene glycol propionaldehyde, containing a single reactive aldehyde, may be used.

An N-terminally monopegylated derivative is preferred for ease in production of a therapeutic. N-terminal pegylation ensures a homogenous product as characterization of the product is simplified relative to di-, tri- or other multi pegylated products. The use of the above reductive alkylation process for preparation of an N-terminal product is preferred for ease in commercial manufacturing.

In yet another aspect of the present invention, provided are methods of using pharmaceutical compositions of the proteins, and derivatives. Such pharmaceutical compositions may be for administration by injection, or for oral, pulmonary, nasal, transdermal or other forms of administration. In general, comprehended by the invention are pharmaceutical compositions comprising effective amounts of protein or derivative products of the invention together with pharmaceutically acceptable diluents, preservatives, solubilizers, emulsifiers, adjuvants and/or carriers. Such compositions include diluents of various buffer content (e.g., Tris-HC1, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Hylauronic acid may also be used, and this may have the effect of promoting sustained duration in the circulation. Such compositions may influence the physical state, stability, rate of in vivo release, and rate of in vivo clearance of the present proteins and derivatives. See, e.g., Remington's Pharmaceutical Sciences, 18$^{th}$ Ed. (1990, Mack Publishing Co., Easton, Pa. 18042) pages 1435–1712 which are herein incorporated by reference. The compositions may be prepared in liquid form, or may be in dried powder, such as lyophilized form. Implantable sustained release formulations are also contemplated, as are transdermal formulations.

Contemplated for use herein are oral solid dosage forms, which are described generally in Remington's Pharmaceutical Sciences, 18$^{th}$ Ed. 1990 (Mack Publishing Co., Easton, Pa. 18042) at Chapter 89, which is herein incorporated by reference. Solid dosage forms include tablets, capsules, pills, troches or lozenges, cachets or pellets. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatized with various polymers (E.g., U.S. Pat. No. 5,013,556). A description of possible solid dosage forms for the therapeutic is given by Marshall, K. In: *Modern Pharmaceutics* Edited by G. S. Banker and C. T. Rhodes Chapter 10, 1979, herein incorporated by reference. In general, the formulation will include the protein (or analog or derivative), and inert ingredients which allow for protection against the stomach environment, and release of the biologically active material in the intestine.

Also specifically contemplated are oral dosage forms of the above derivatized proteins. Protein may be chemically modified so that oral delivery of the derivative is efficacious. Generally, the chemical modification contemplated is the attachment of at least one moiety to the protein (or peptide) molecule itself, where said moiety permits (a) inhibition of proteolysis; and (b) uptake into the blood stream from the stomach or intestine. Also desired is the increase in overall stability of the protein and increase in circulation time in the body. Examples of such moieties include: Polyethylene glycol, copolymers of ethylene glycol and propylene glycol, carboxymethyl cellulose, dextran, polyvinyl alcohol, polyvinyl pyrrolidone and polyproline. Abuchowski and Davis, Soluble Polymer-Enzyme Adducts. In: "Enzymes as Drugs", Hocenberg and Roberts, eds., Wiley-Interscience, New York, N.Y. (1981), pp 367–383; Newmark, et al., J. Appl. Biochem. 4: 185–189 (1982). Other polymers that could be used are poly-1,3-dioxolane and poly-1,3,6-tioxocane.

For the protein (or derivative) the location of release may be the stomach, the small intestine (the duodenum, the jejunem, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the protein (or derivative) or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic, i.e., powder; for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multiparticulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the protein (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, α-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An antifrictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the protein or derivative either alone or as a mixture in different ratios.

Additives which potentially enhance uptake of the protein (or derivative) are for instance the fatty acids oleic acid, linoleic acid and linolenic acid.

Controlled release formulation may be desirable. The drug could be incorporated into an inert matrix which permits release by either diffusion or leaching mechanisms, i.e., gums. Slowly degenerating matrices may also be incorporated into the formulation. Another form of a controlled release of this therapeutic is by a method based on the Oros therapeutic system (Alza Corp.), i.e., the drug is enclosed in a semipermeable membrane which allows water to enter and push drug out through a single small opening due to osmotic effects. Some entric coatings also have a delayed release effect.

Other coatings may be used for the formulation. These include a variety of sugars which could be applied in a coating pan. The therapeutic agent could also be given in a film coated tablet and the materials used in this instance are divided into 2 groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxymethyl cellulose, providone and the prolyethylene glycols. The second group consists of the enteric materials that are commonly esters of phthalic acid.

A mix of materials might be used to provide the optimum film coating. Film coating may be carried out in a pan coater or in a fluidized bed or by compression coating.

Also contemplated herein is pulmonary delivery of the present protein, or derivative thereof. The protein (derivative) is delivered to the lungs of a mammal while inhaling and traverses across the lung epithelial lining to the blood stream. (Other reports of this include Adjei et al., Pharmaceutical Research 7: 565–569 (1990); Adjei et al., International Journal of Pharmaceutics 63: 135–144 (1990) (leuprolide acetate); Braquet et al., Journal of Cardiovascular Pharmacology 13 (suppl. 5): s. 143–146 (1989) (endothelin-1); Hubbard et al., Annals of Internal Medicine 3: 206–212 (1989) α1-antitrypsin); Smith et al., J. Clin. Invest. 84: 1145–1146 (1989) (α-1-proteinase); Oswein et al., "Aerosolization of Proteins", Proceedings of Symposium on Respiratory Drug Delivery II, Keystone, Colo., March, 1990 (recombinant human growth hormone); Debs et al., The Journal of Immunology 140: 3482–3488 (1988) (interferon-γ and tumor necrosis factor alpha) and Platz et al., U.S. Pat. No. 5,284,656 (granulocyte colony stimulating factor).

Contemplated for use in the practice of this invention are a wide range of mechanical devices designed for pulmonary delivery of therapeutic products, including but not limited to nebulizers, metered dose inhalers, and powder inhalers, all of which are familiar to t hose skilled in the art.

Some specific examples of commercially available devices suitable for the practice of t his invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of protein (or analog or derivative). Typically, each formulation is specific to the type of device employed and may involve the use of an appropriate propellant material, in addition to diluents, adjuvants and/or carriers useful in therapy.

The protein (or derivative) should most advantageously be prepared in particulate form with an average particle size of less than 10 μm (or microns), most preferably 0.5 to 5 μm, for most effective delivery to the distal lung.

Carriers include carbohydrates such as trehalose, mannitol, xylitol, sucrose, lactose, and sorbitol. Other ingredients for use in formulations may include DPPC, DOPE, DSPC and DOPC. Natural or synthetic surfactants may be used. Polyethylene glycol may be used (even apart from its use in derivatizing the protein or analog). Dextrans, such as cyclodextran, may be used. Bile salts and other related enhancers m ay be used. Cellulose and cellulose derivatives may be used. Amino acids may be used, such as use in a buffer formulation.

Also, the use of liposomes, microcapsules or microspheres, inclusion complexes, or other types of carriers is contemplated.

Formulations suitable for use with a nebulizer, either jet or ultrasonic, will typically comprise protein (or derivative) dissolved in water at a concentration of about 0.1 to 25 mg of biologically active protein per mL of solution. The formulation may also include a buffer and a simple sugar (e.g., for protein stabilization and regulation of osmotic pressure). The nebulizer formulation may also contain a surfactant, to reduce or prevent surface induced aggregation of the protein caused by atomization of the solution in forming the aerosol.

Formulations for use with a metered-dose inhaler device will generally comprise a finely divided powder containing the protein (or derivative) suspended in a propellant with the aid of a surfactant. The propellant may be any conventional material employed for t his purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing protein (or derivative) and may also include a bulking agent, such as lactose, sorbitol, sucrose, mannitol, trehalose, or xylitol in amounts which facilitate dispersal of the powder from the device, e.g., 50 to 90% by weight of the formulation.

Nasal delivery of the protein (or analog or derivative) is also contemplated. Nasal delivery allows the passage of the protein to the blood stream directly after administering the therapeutic product to the nose, without the necessity for deposition of the product in the lung. Formulations for nasal delivery include those with dextran or cyclodextran. Delivery via transport across other mucus membranes is also contemplated.

One skilled in the art will be able to ascertain effective dosages by administration and observing the desired therapeutic effect. Preferably, the formulation of the molecule will be such that between about 0.10 µg/kg/day and 10 mg/kg/day will yield the desired therapeutic effect. The effective dosages may be determined using diagnostic tools over time. For example, a diagnostic for measuring the amount of OB protein in the blood (or plasma or serum) may first be used to determine endogenous levels of OB protein. Such diagnostic tool may be in the form of an antibody assay, such as an antibody sandwich assay. The amount of endogenous OB protein is quantified initially, and a baseline is determined. The therapeutic dosages are determined as the quantification of endogenous and exogenous OB protein (that is, protein, analog or derivative found within the body, either self-produced or administered) is continued over the course of therapy. The dosages may therefore vary over the course of therapy, with a relatively high dosage being used initially, until therapeutic benefit is seen, and lower dosages used to maintain the therapeutic benefits.

Ideally, in situations where solely an increase in lean body mass is desired, the dosage will be insufficient to result in weight loss. Thus, during an initial course of therapy of an obese person, dosages may be administered whereby weight loss and concomitant fat tissue decrease/lean mass increase is achieved. Once sufficient weight loss is achieved, a dosage sufficient to prevent re-gaining weight, yet sufficient to maintain desired lean mass increase (or, prevention of lean mass depletion) may be administered. These dosages can be determined empirically, as the effects of OB protein are reversible. E.g., Campfield et al., Science 269: 546–549 (1995) at 547. Thus, if a dosage resulting in weight loss is observed when weight loss is not desired, one would administer a lower dose in order to achieve the desired increase in lean tissue mass, yet maintain the desired weight.

For increasing an individual's sensitivity to insulin, similar dosage considerations may be taken into account. Lean mass increase without weight loss may be achieved sufficient to decrease the amount of insulin (or, potentially, amylin or other potential diabetes treating drugs) an individual would be administered for the treatment of diabetes.

For increasing overall strength, there may be similar dosage considerations. Lean mass increase with concomitant increase in overall strength may be achieved with doses insufficient to result in weight loss. Other benefits, such as an increase in red blood cells (and oxygenation in the blood) and a decrease in bone resorption or osteoporosis may also be achieved in the absence of weight loss.

The present methods may be used in conjunction with other medicaments, such as those useful for the treatment of diabetes (e.g., insulin, and possibly amylin), cholesterol and blood pressure lowering medicaments (such as those which reduce blood lipid levels or other cardiovascular medicaments), and activity increasing medicaments (e.g., amphetamines). Appetite suppressants may also be used. Such administration may be simultaneous or may be in seriatim.

In addition, the present methods may be used in conjunction with surgical procedures, such as cosmetic surgeries designed to alter the overall appearance of a body (e.g., liposuction or laser surgeries designed to reduce body mass, or implant surgeries designed to increase the appearance of body mass). The health benefits of cardiac surgeries, such as bypass surgeries or other surgeries designed to relieve a deleterious condition caused by blockage of blood vessels by fatty deposits, such as arterial plaque, may be increased with concomitant use of the present compositions and methods. Methods to eliminate gall stones, such as ultrasonic or laser methods, may also be used either prior to, during or after a course of the present therapeutic methods. Furthermore, the present methods may be used as an adjunct to surgeries or therapies for broken bones, damaged muscle, or other therapies which would be improved by an increase in lean tissue mass.

Therefore, the present invention provides a method for increasing lean tissue mass, comprised of administering an effective amount of an OB protein, analog or derivative thereof selected from among:

(a) the amino acid sequence 1–146 as set forth in SEQ ID NO: 2 (below) or SEQ ID NO: 4 (below), (b) the amino acid sequence set 1–146 as set forth in SEQ ID NO: 4 (below) having a lysine residue at position 35 and an isoleucine residue at position 74;

(c) the amino acid sequence of subpart (b) having a different amino acid substituted in one or more of the following positions (using the numbering according to SEQ ID NO: 4, and retaining the same numbering even in the absence of a glutaminyl residue at position 28): 4, 8, 32, 33, 35, 48, 50, 53, 60, 64, 66, 67, 68, 71, 74, 77, 78, 89, 97, 100, 102, 105, 106, 107, 108, 111, 112, 118, 136, 138, 142, and 145;

(d) the amino acid sequence of subparts (a), (b) or (c) optionally lacking a glutaminyl residue at position 28;

(e) the amino acid sequence of subparts (a), (b), (c), or (d) having a methionyl residue at the N terminus.

(f) a truncated OB protein analog selected from among: (using the numbering of SEQ ID NO: 4 having a lysine residue at position 35 and an isoleucine residue at position 74):

(i) amino acids 98–146;
(ii) amino acids 1–32;
(iii) amino acids 40–116;
(iv) amino acids 1–99 and 112–146;
(v) amino acids 1–99 and 112–146 having one or more of amino acids 100–111 sequentially placed between amino acids 99 and 112; and,
(vi) the truncated OB analog of subpart (i) having one or more of amino acids 100, 102, 105, 106, 107, 108, 111, 112, 118, 136, 138, 142, and 145 substituted with another amino acid;
(vii) the truncated analog of subpart (ii) having one or more of amino acids 4, 8 and 32 substituted with another amino acid;
(viii) the truncated analog of subpart (iii) having one or more of amino acids 50, 53, 60, 64, 66, 67, 68, 71, 74, 77, 78, 89, 97, 100, 102, 105, 106, 107, 108, 111 and 112 replaced with another amino acid;
(ix) the truncated analog of subpart (iv) having one or more of amino acids 4, 8, 32, 33, 35, 48, 50, 53, 60, 64, 66, 67, 68, 71, 74, 77, 78, 89, 97, 112, 118, 136, 138, 142, and 145 replaced with another amino acid;

(x) the truncated analog of subpart (v) having one or more of amino acids 4, 8, 32, 33, 35, 48, 50, 53, 60, 64, 66, 67, 68, 71, 74, 77, 78, 89, 97, 100, 102, 105, 106, 107, 108, 111, 112, 118, 136, 138, 142, and 145 replaced with another amino acid;

(xi) the truncated analog of any of subparts (i)-(x) having an N-terminal methionyl residue; and (g) the OB protein or analog derivative of any of subparts (a) through (f) comprised of a chemical moiety connected to the protein moiety;

(h) a derivative of subpart (g) wherein said chemical moiety is a water soluble polymer moiety;

(i) a derivative of subpart (h) wherein said water soluble polymer moiety is polyethylene glycol;

(j) a derivative of subpart (h)herein said water soluble polymer moiety is a polyamino acid moiety;

(k) a derivative of subpart (h) wherein said water soluble polymer moiety is attached at solely the N-terminus of said protein moiety;

(l) an OB protein, analog or derivative of any of subparts (a) through (k) in a pharmaceutically acceptable carrier.

The following examples are offered to more fully illustrate the invention, but are not to be construed as limiting the scope thereof. Example 1 demonstrates that OB protein is effective for increasing lean mass in non-obese animals. Example 2 demonstrates that OB protein is effective for increasing lean mass in obese primates. Example 3 through 5 are prophetic examples of human use. Materials and Methods follow.

EXAMPLE 1

These data demonstrate that the OB protein, or analogs or derivatives thereof, is effective for increasing lean mass.

Recombinant methionyl murine OB protein (as described below) was continuously administered via osmotic pump infusion for a period of four weeks. Table 1 data show the average body composition (for CD1 mice) at the dosages indicated:

TABLE 1

| Dose (mg/kg/day) | Water (g) | Fat (g) | Lean Mass (g) |
|---|---|---|---|
| PBS | 22.13 +/− .33 | 8.39 +/− .67 | 3.2 +/− .28 |
| 0.03 | 22.09 +/− .55 | 9.44 +/− .61 | 2.32 +/− .54 |
| 0.1 | 21.02 +/− .44 | 6.64 +/− −1 | 3.85 +/− .57 |
| 0.3 | 22.02 +/− .31 | 5.22 +/− .91 | 4.72 +/− .48 |
| 1.0 | 21.34 +/− .38 | 1.51 +/− .48 | 6.94 +/− .25 |

In non-obese CD1 mice, recombinant methionyl murine OB protein continuously administered at a dose of either 0.3 or 1 mg/kg/day was shown to effect an increase in lean mass relative to the control animals, who were administered PBS.

EXAMPLE 2

This Example demonstrates that recombinant methionyl human OB protein causes lean tissue mass increase in primates.

Obese cynomolgus monkeys having greater than 20% body fat were administered recombinant methionyl human OB protein subcutaneously, at a daily dose of 1 mg protein/kg body weight/day (see Materials and Methods, below). Control animals were administered phosphate buffered saline. Body composition was performed using Dual Energy X-Ray Absorptimetry ("DEXA") analysis. Measurements of body composition were taken at 7-day intervals.

Tables 2A and 2B show the results of body composition analysis in terms of mass of fat or lean tissue. Data are presented in grams. Results for the 2 control animals are in Table 2A. The data for 4 test animals are presented in Table 2B. (Data for bone mass are also presented). As can be seen, at day 28, the test animals lost approximately 264 grams of fat, and gained approximately 138 grams of lean mass. At day 28, the controls lost 36 grams of fat tissue and gained approximately 25 grams of lean mass. This demonstrates that OB protein causes an increase in lean tissue mass.

TABLE 2A

| Control (n = 2) | Baseline | Day 7 | Day 14 | Day 21 | Day 28 |
|---|---|---|---|---|---|
| Lean Mass ± STD Dev | 5393 ± 894 | 5411 ± 863 | 5467 ± 934 | 5410 ± 983 | 5418 ± 802 |
| Fat Mass ± STD Dev | 2884 ± 1962 | 2838 ± 1936 | 2835 ± 2113 | 2852 ± 2271 | 2848 ± 2122 |
| Bone Mass ± STD Dev | 325 ± 12 | 324 ± 4 | 324 ± 11 | 325 ± 16 | 321 ± 7 |

TABLE 2B

| OB Protein (n = 4) | Baseline | Day 7 | Day 14 | Day 21 | Day 28 |
|---|---|---|---|---|---|
| Lean Mass ± STD Dev | 4877 ± 960 | 4782 ± 927 | 4899 ± 1037 | 4957 ± 1053 | 5015* ± 1192 |
| Fat Mass ± STD Dev | 2577 ± 1927 | 2536 ± 1982 | 2432 ± 1874 | 2380 ± 1924 | 2313* ± 1903 |
| Bone Mass ± STD Dev | 296 ± 96 | 296 ± 99 | 294 ± 97 | 292 ± 96 | 291 ± 96 |

*indicates p-value less than 0.05 for repeated measures ANOVA

EXAMPLE 3

A non-obese human patient desires an increase in lean tissue mass for therapeutic purposes, such as recovery from illness which depleted lean tissue mass. The patient is administered an effective amount of OB protein, analog or derivative thereof to result in the desired increase in lean tissue mass. Increase in lean tissue mass is monitored using DEXA scanning. Levels of circulating OB protein or analog or derivative may be monitored using a diagnostic kit, such as an antibody assay against the OB protein (or other antigenic source if applicable).

EXAMPLE 4

A human subject desires an increase in lean tissue mass for cosmetic or athletic purposes, such as an increase in lean tissue in order to improve outward appearance. The patient is administered an effective amount of OB protein, analog or derivative thereof to result in the desired increase in lean tissue mass. Increase in lean tissue mass is monitored using DEXA scanning. Oxygen levels in the blood increase. Levels of circulating OB protein or analog or derivative may be monitored using a diagnostic kit, such as an antibody assay against the OB protein (or other antigenic source if applicable).

EXAMPLE 5

A diabetic human patient desires to use decreased dosages of insulin for treatment of diabetes. The patient is administered an effective amount of OB protein, analog or derivative thereof to result in an increase in lean tissue mass. The patient's sensitivity to insulin increases, and the dosage of insulin necessary to alleviate symptoms of diabetes is decreased, either in terms of a decrease in the units of insulin needed, or in terms of a decrease in the number of injections of insulin needed per day. Levels of circulating OB protein or analog or derivative may be monitored using a diagnostic kit, such as an antibody assay against the OB protein (or other antigenic source if applicable).

EXAMPLE 6

A non-obese elderly human patient desires an increase in overall strength. The patient is administered an effective amount of OB protein, analog or derivative thereof to result in an increase in lean tissue mass, and increase in overall strength. Bone resorption is also decreased, and an osteoporosis condition is improved. Levels of circulating OB protein or analog or derivative may be monitored using a diagnostic kit, such as an antibody assay against the OB protein (or other antigenic source if applicable).

Materials and Methods

Animals:

Rodents. Wild type CD1 mice were used for Example 1 (Table 1 data). Animals were maintained under humane conditions.

Primates. A total of six cynomolgus monkeys were used. All monkeys were at least 20% fat at the outset of the study. Animals were randomized for weight, and four animals were tested with OB protein, two animals were controls.

Administration of Protein or Vehicle.

For Rodents. For Example 1, (Table 1 data) recombinant murine protein (as described below) or vehicle (phosphate buffered saline, "PBS," pH 7.4) was administered by osmotic pump infusion. Alzet osmotic minipumps (Alza, Palo Alto, Calif., model no. 2002) were surgically placed in each mouse in a subcutaneous pocket in the subscapular area, and replaced after two weeks. The pumps were calibrated to administer 0.5μ protein in solution per hour for the dosages indicated in Table 1.

For Primates. For Example 2, recombinant methionyl human OB protein (of SEQ ID NO: 4 having a lysine at position 35 and an isoleucine at position 74), dosed at 1 mg/ml PBS, was administered subcutaneously at a dose of 1 mg protein/kg body weight/day. Control animals were administered PBS in the same fashion.

Rodent Carcass Analysis. Carcass analysis was conducted as in A. I. Leshner, V. A. Litwin, and R. L. Squibb, Brain Res. 9: 281 (1972). Water composition was determined by subtraction of carcass weight before and after a 4-day dehydration period. Fat was extracted from a pre-weighed portion of the ground, dried carcass with ethyl ether and ethyl alcohol, so that percent fact could be calculated from the amount of material remaining after the extraction procedure. Lean mass was defined as the proportion of ground carcass that remained after dehydration and ether extraction.

Primate Dual Energy X-Ray Absortimetry Scanning: "DEXA" scanning was performed at the time points indicated in Table 2 A and B, in Example 2.

Protein: Sequence ID Nos. 1 and 2 set forth murine recombinant OB DNA and protein, and Sequence ID Nos. 3 and 4 set forth an analog recombinant human OB DNA and protein. Murine recombinant protein as in SEQ ID NO: 2 was used in EXAMPLE 1. Recombinant human OB protein as in SEQ ID NO: 4 having a lysine residue at position 35 and an isoleucine residue at position 74 was used in EXAMPLE 2. As indicated above, the below murine and human analog recombinant proteins are illustrative of the OB protein which may be used in the present methods of treatment and manufacture of a medicament. Other OB proteins and analogs or derivatives thereof may be used.

Herein, the first amino acid of the amino acid sequence for recombinant protein is referred to as +1, and is valine, and the amino acid at position −1 is methionine. The C-terminal amino acid is number 146 (cysteine).

Recombinant murine met OB (double stranded) DNA and amino acid sequence (Seq. ID. Nos. 1 and 2):

```
    TCTAGATTTGAGTTTTAACTTTTAGAAGGAGGAATAACATATGGTACCGATCCAGAAAGT
 9 -+---------+---------+---------+---------+---------+--------  68
    AGATCTAAACTCAAAATTGAAATCTTCCTCCTTATTGTATACCATGGCTAGGTCTTTCA
                                           M  V  P  I  Q  K  V -

TCAGGACGACACCAAAACCTTAATTAAAACGATCGTTACGCGTATCAACGACATCAGTCA
69 -+---------+---------+---------+---------+---------+--------  128
    AGTCCTGCTGTGGTTTTGGAATTAATTTTGCTAGCAATGCGCATAGTTGCTGTAGTCAGT
     Q  D  D  T  K  T  L  I  K  T  I  V  T  R  I  N  D  I  S  H -
```

```
     CACCCAGTCGGTCTCCGCTAAACAGCGTGTTACCGGTCTGGACTTCATCCCGGGTCTGCA
129 -+---------+---------+---------+---------+---------+--------  188
     GTGGGTCAGCCAGAGGCGATTTGTCGCACAATGGCCAGACCTGAAGTAGGGCCCAGACGT
      T   Q   S   V   S   A   K   Q   R   V   T   G   L   D   F   I   P   G   L   H -

CCCGATCCTAAGCTTGTCCAAAATGGACCAGACCCTGGCTGTATACCAGCAGGTGTTAAC
189 -+---------+---------+---------+---------+---------+--------  248
     GGGCTAGGATTCGAACAGGTTTTACCTGGTCTGGGACCGACATATGGTCGTCCACAATTG
        P   I   L   S   L   S   K   M   D   Q   T   L   A   V   Y   Q   Q   V   L   T -

CTCCCTGCCGTCCCAGAACGTTCTTCAGATCGCTAACGACCTCGAGAACCTTCGCGACCT
249 -+---------+---------+---------+---------+---------+--------  308
     GAGGGACGGCAGGGTCTTGCAAGAAGTCTAGCGATTGCTGGAGCTCTTGGAAGCGCTGGA
        S   L   P   S   Q   N   V   L   Q   I   A   N   D   L   E   N   L   R   D   L -

GCTGCACCTGCTGGCATTCTCCAAATCCTGCTCCCTGCCGCAGACCTCAGGTCTTCAGAA
309 -+---------+---------+---------+---------+---------+--------  368
     CGACGTGGACGACCGTAAGAGGTTTAGGACGAGGGACGGCGTCTGGAGTCCAGAAGTCTT
        L   H   L   L   A   F   S   K   S   C   S   L   P   Q   T   S   G   L   Q   K -

ACCGGAATCCCTGGACGGGGTCCTGGAAGCATCCCTGTACAGCACCGAAGTTGTTGCTCT
369 -+---------+---------+---------+---------+---------+--------  428
     TGGCCTTAGGGACCTGCCCCAGGACCTTCGTAGGGACATGTCGTGGCTTCAACAACGAGA
        P   E   S   L   D   G   V   L   E   A   S   L   Y   S   T   E   V   V   A   L -

GTCCCGTCTGCAGGGTTCCCTTCAGGACATCCTTCAGCAGCTGGACGTTTCTCCGGAATG
429 -+---------+---------+---------+---------+---------+--------  488
     CAGGGCAGACGTCCCAAGGGAAGTCCTGTAGGAAGTCGTCGACCTGCAAAGAGGCCTTAC
        S   R   L   Q   G   S   L   Q   D   I   L   Q   Q   L   D   V   S   P   E   C -

TTAATGGATCC
489 -+---------
     AATTACCTAGG
```

Recombinant human met OB analog (Double Stranded) DNA and amino acid sequence (SEQ. ID. Nos. 3 and 4)

```
     CATATGGTACCGATCCAGAAAGTTCAGGACGACACCAAAACCTTAATTAAAACGATCGTT
  1 ---------+---------+---------+---------+---------+----------  60
     GTATACCATGGCTAGGTCTTTCAAGTCCTGCTGTGGTTTTGGAATTAATTTTGCTAGCAA
         M   V   P   I   Q   K   V   Q   D   D   T   K   T   L   I   K   T   I   V -

ACGCGTATCAACGACATCAGTCACACCCAGTCGGTGAGCTCTAAACAGCGTGTTACAGGC
 61 ---------+---------+---------+---------+---------+----------  120
     TGCGCATAGTTGCTGTAGTCAGTGTGGGTCAGCCACTCGAGATTTGTCGCACAATGTCCG
      T   R   I   N   D   I   S   H   T   Q   S   V   S   S   K   Q   R   V   T   G -

CTGGACTTCATCCCGGGTCTGCACCCGATCCTGACCTTGTCCAAAATGGACCAGACCCTG
121 ---------+---------+---------+---------+---------+----------  180
     GACCTGAAGTAGGGCCCAGACGTGGGCTAGGACTGGAACAGGTTTTACCTGGTCTGGGAC
      L   D   F   I   P   G   L   H   P   I   L   T   L   S   K   M   D   Q   T   L -

GCTGTATACCAGCAGATCTTAACCTCCATGCCGTCCCGTAACGTTCTTCAGATCTCTAAC
181 ---------+---------+---------+---------+---------+----------  240
     CGACATATGGTCGTCTAGAATTGGAGGTACGGCAGGGCATTGCAAGAAGTCTAGAGATTG
      A   V   Y   Q   Q   I   L   T   S   M   P   S   R   N   V   L   Q   I   S   N -

GACCTCGAGAACCTTCGCGACCTGCTGCACGTGCTGGCATTCTCCAAATCCTGCCACCTG
241 ---------+---------+---------+---------+---------+----------  300
     CTGGAGCTCTTGGAAGCGCTGGACGACGTGCACGACCGTAAGAGGTTTAGGACGGTGGAC
      D   L   E   N   L   R   D   L   L   H   V   L   A   F   S   K   S   C   H   L -

CCATGGGCTTCAGGTCTTGAGACTCTGGACTCTCTGGGCGGGGTCCTGGAAGCATCCGGT
301 ---------+---------+---------+---------+---------+----------  360
     GGTACCCGAAGTCCAGAACTCTGAGACCTGAGAGACCCGCCCCAGGACCTTCGTAGGCCA
      P   W   A   S   G   L   E   T   L   D   S   L   G   G   V   L   E   A   S   G -

TACAGCACCGAAGTTGTTGCTCTGTCCCGTCTGCAGGGTTCCCTTCAGGACATGCTTTGG
361 ---------+---------+---------+---------+---------+----------  420
     ATGTCGTGGCTTCAACAACGAGACAGGGCAGACGTCCCAAGGGAAGTCCTGTACGAAACC
      Y   S   T   E   V   V   A   L   S   R   L   Q   G   S   L   Q   D   M   L   W -

CAGCTGGACCTGTCTCCGGGTTGTTAATGGATCC
421 ---------+---------+---------+----  454
     GTCGACCTGGACAGAGGCCCAACAATTACCTAGG
      Q   L   D   L   S   P   G   C   *
```

Methods for Production

The below methods for production have been used to produce biologically active recombinant methionyl murine or human analog OB protein. Similar methods may be used to prepare biologically active recombinant methionyl human OB protein.

Expression Vector and Host Strain

The plasmid expression vector used is pCFM1656, ATCC Accession No. 69576. The above DNA was ligated into the expression vector pCFM1656 linearized with XbaI and BamHI and transformed into the E. coli host strain, FM5. E. coli FM5 cells were derived at Amgen Inc., Thousand Oaks, Calif. from E. coli K-12 strain (Bachmann, et al., Bacteriol. Rev. 40: 116–167 (1976)) and contain the integrated lambda phage repressor gene, $cI_{857}$ (Sussman et al., C. R. Acad. Sci. 254: 1517–1579 (1962)). Vector production, cell transformation, and colony selection were performed by standard methods. E.g., Sambrook, et al., Molecular Cloning: A Laboratory Manual, 2d Edition, Cold Spring Harbor Laboratory Press. Cold Spring Harbor, N.Y. Host cells were grown in LB media.

Fermentation Process. A three-phase fermentation protocol known as a fed-batch process was used. Media compositions are set forth below.

Batch: A nitrogen and phosphate source were sterilized (by raising to 122° C. for 35 minutes, 18–20 psi) in the fermentation vessel (Biolafitte, 12 liter capacity). Upon cooling, carbon, magnesium, vitamin and trace metal sources were aseptically. An overnight culture of the above recombinant murine protein-producing bacteria (16 hours or more) of 500 mL (grown in LB broth) was added to the fermentor.

Feed I: Upon reaching between 4.0–6.0 $OD_{600}$, cultures were fed with Feed I. The glucose was fed at a limiting rate in order to control the growth rate (p). An automated system (called the Distributive Control System) was instructed to control the growth rate to 0.15 generations per hour.

Feed II: When the $OD_{600}$ had reached 30, culture temperatures were slowly increased to 42° C. and the feed changed to Feed II, below. The fermentation was allowed to continue for 10 hours with sampling every 2 hours. After 10 hours, the contents of the fermentor was chilled to below 20° C. and harvested by centrifugation.

Media Composition:

| Batch: | 10 g/L | Yeast extract |
|---|---|---|
| | 5.25 g/L | $(NH_4)_2SO_4$ |
| | 3.5 g/L | $K_2HPO_4$ |
| | 4.0 g/L | $KH_2PO_4$ |
| | 5.0 g/L | Glucose |
| | 1.0 g/L | $MgSO_4.7H_2O$ |
| | 2.0 mL/L | Vitamin Solution |
| | 2.0 mL/L | Trace Metal Solution |
| | 1.0 mL/L | P2000 Antifoam |
| Feed I: | 50 g/L | Bacto-tryptone |
| | 50 g/L | Yeast extract |
| | 450 g/L | Glucose |
| | 8.75 g/L | $MgSO_4.7H_2O$ |
| | 10 mL/L | Vitamin Solution |
| | 10 mL/L | Trace Metal Solution |
| Feed II: | 200 g/L | Bacto-tryptone |
| | 100 g/L | Yeast extract |
| | 110 g/L | Glucose |

Vitamin Solution (Batch and Feed I): 0.5 g Biotin, 0.4 g Folic acid, and 4.2 g riboflavin, was dissolved in 450 mls $H_2O$ and 3 mls 10 N NaOH, and brought to 500 mLs in $H_2O$. 14 g pyridoxine-HCl and 61 g niacin was dissolved 150 ml $H_2O$ and 50 ml 10 N NaOH, and brought to 250 ml in $H_2O$. 54 g panothenic acid was dissolved in 200 mL $H_2O$, and brought to 250 mL. The three solutions were combined and brought to 10 liters total volume.

Trace Metal Solution (Batch and Feed I):

Ferric Chloride ($FeCl_3.6H_2O$): 27 g/L

Zinc Chloride ($ZnCL_2.4H_2O$): 2 g/L

Cobalt Chloride ($COCl_2. 6H_2O$): 2 g/L

Sodium Molybdate ($NaMoO_4.2H_2O$): 2 g/L

Calcium Chloride ($CaCl_2.2H_2O$): 1 g/L

Cupric Sulfate ($CuSO_4.5H_2O$): 1.9 g/L

Boric Acid ($H_3BO_3$): 0.5 g/L

Manganese Chloride ($MnCl_2.4H_2O$): 1.6 g/L

Sodium Citrate dehydrate: 73.5 g/L

Purification Process for Murine OB Protein

Purification was accomplished by the following steps (unless otherwise noted, the following steps were performed at 4° C.):

1. Cell paste. E. coli cell paste was suspended in 5 times volume of 7 mM of EDTA, pH 7.0. The cells in the EDTA were further broken by two passes through a microfluidizer. The broken cells were centrifuged at 4.2 K rpm for 1 hour in a Beckman J6-B centrifuge with a JS-4.2 rotor.

2. Inclusion body wash #1. The supernatant from above was removed, and the pellet was resuspended with 5 times volume of 7 mM EDTA, pH 7.0, and homogenized. This mixture was centrifuged as in step 1.

3. Inclusion body wash #2. The supernatant from above was removed, and the pellet was resuspended in ten times volume of 20 mM tris, pH 8.5, 10 mM DTT, and 1% deoxycholate, and homogenized. This mixture was centrifuged as in step 1.

4. Inclusion body wash #3. The supernatant from above was removed and the pellet was resuspended in ten times volume of distilled water, and homogenized. This mixture was centrifuged as in step 1.

5. Refolding. The pellet was refolded with 15 volumes of 10 mM HEPES, pH 8.5, 1% sodium sarcosine (N-lauroyl sarcosine), at room temperature. After 60 minutes, the solution was made to be 60 μm copper sulfate, and then stirred overnight.

6. Removal of sarcosine. The refolding mixture was diluted with 5 volumes of 10 mM tris buffer, pH 7.5, and centrifuged as in step 1. The supernatant was collected, and mixed with agitation for one hour with Dowex® 1-X4 resin (Dow Chemical Co., Midland Mich.), 20–50 mesh, chloride form, at 0.066% total volume of diluted refolding mix. See WO 89/10932 at page 26 for more information on Dowex®. This mixture was poured into a column and the eluant collected. Removal of sarcosine was ascertained by reverse phase HPLC.

7. Acid precipitation. The eluant from the previous step was collected, and pH adjusted to pH 5.5, and incubated for 30 minutes at room temperature. This mixture was centrifuged as in step 1.

8. Cation exchange chromatography. The pH of the supernatant from the previous step was adjusted to pH 4.2, and loaded on CM Sepharose Fast Flow (at 7% volume). 20 column volumes of salt gradient were done at 20 mM NsOAC, pH 4.2, 0 M to 1.0 M NaCl.

9. Hydrophobic interaction chromatography. The CM Sepharose pool of peak fractions (ascertained from ultraviolet absorbance) from the above step was made to be 0.2 M ammonium sulfate. A 20 column volume reverse salt gradient was done at 5 mM NaOAC, pH 4.2, with 0.4 M to 0 M ammonium sulfate. This material was concentrated and diafiltered into PBS.

Fermentation of recombinant human OB protein analog: Fermentation of the above host cells to produce recombinant human OB protein analog (SEQ ID NO: 4) can be accomplished using the conditions and compositions as described above for recombinant murine material.

Purification of the recombinant human OB protein analog: Recombinant human protein analog may be purified using methods similar to those used for purification of recombinant murine protein, as in Example 1, above. For preparation of recombinant human OB protein analog, step 8 should be performed by adjusting the pH of the supernatant from step 7 to pH 5.0, and loading this onto a CM Sepharose fast flow column. The 20 column volume salt gradient should be performed at 20 mM NaOAC, pH 5.5, 0M to 0.5 M NaCl. Step 9 should be performed by diluting the CM Sepharose pool four fold with water, and adjusting the pH to 7.5. This mixture should be made to 0.7 M ammonium sulfate. Twenty column volume reverse salt gradient should be done at 5 mM NaOAC, pH 5.5, 0.2 M to 0M ammonium sulfate. Otherwise, the above steps are identical. For EXAMPLE 2 material, the recombinant human OB protein of SEQ ID NO: 4 having lysine 35 and isoleucine 74 was formulated in a buffer containing 10 mM histidine, 4.3% arginine, at pH 6.0.

While the present invention has been described in terms of preferred embodiments, it is understood that variations and modifications will occur to those skilled in the art. Therefore, it is intended that the appended claims cover all such equivalent variations which come within the scope of the invention as claimed.

The invention claimed is:

1. An isolated fusion protein comprising an Fc portion of an antibody attached at the N-terminus of an OB protein of SEQ ID NO: 2.

2. An isolated fusion protein comprising an Fc portion of an antibody attached at the N-terminus of an OB protein of SEQ ID NO: 4.

3. The isolated fusion protein of claim 2, wherein, in the 146 residue sequence of SEQ ID NO: 4, lysine is substituted at position 35 and isoleucine is substituted at position 74.

4. The isolated fusion protein of claim 2, wherein the Fc portion and the OB protein are attached via a linker.

* * * * *

UNITED STATES PATENT AND TRADEMARK OFFICE
CERTIFICATE OF CORRECTION

PATENT NO. : 7,208,577 B2  Page 1 of 1
APPLICATION NO. : 11/033600
DATED : April 24, 2007
INVENTOR(S) : Mary Ann Pelleymounter et al.

It is certified that error appears in the above-identified patent and that said Letters Patent is hereby corrected as shown below:

Col. 28, lines 51-52
In the claims, please insert the following:

5. The isolated fusion protein of claim 1, wherein he Fc portion and the OB protein are attached via a linker.

Signed and Sealed this

Twenty-seventh Day of May, 2008

JON W. DUDAS
*Director of the United States Patent and Trademark Office*